United States Patent
Wieland et al.

(10) Patent No.: US 6,812,709 B2
(45) Date of Patent: Nov. 2, 2004

(54) SENSOR FOR MEASURING THE ELECTRICAL CONDUCTIVITY OF A FLUID MEDIUM

(75) Inventors: Christoph Wieland, Böblingen (DE); Armin Zeller, Ditzingen (DE)

(73) Assignee: Endress + Hauser Conducta Gesellschaft für Mess- und Regeltechnik mbH + Co., Gerlingen (DE)

( * ) Notice: Subject to any disclaimer, the term of this patent is extended or adjusted under 35 U.S.C. 154(b) by 1 day.

(21) Appl. No.: 10/434,183

(22) Filed: May 9, 2003

(65) Prior Publication Data

US 2003/0197499 A1 Oct. 23, 2003

Related U.S. Application Data

(63) Continuation of application No. 09/435,784, filed on Nov. 8, 1999, now abandoned.

(30) Foreign Application Priority Data

Nov. 6, 1998 (DE) .......................................... 198 51 146

(51) Int. Cl.[7] ............................................. G01N 27/02
(52) U.S. Cl. ..................................................... 324/445
(58) Field of Search ................................. 324/439, 442, 324/445, 543, 544, 551

(56) References Cited

U.S. PATENT DOCUMENTS

| | | | | |
|---|---|---|---|---|
| 2,542,057 A | * | 2/1951 | Relis | 324/445 |
| 4,220,920 A | * | 9/1980 | Gross | 324/442 |
| 4,958,523 A | * | 9/1990 | Knaak | 73/861.11 |
| 5,266,899 A | * | 11/1993 | Bull et al. | 324/439 |
| 6,087,836 A | * | 7/2000 | Divljakovic et al. | 324/557 |

* cited by examiner

*Primary Examiner*—Evan Pert
*Assistant Examiner*—Paresh Patel
(74) *Attorney, Agent, or Firm*—Paul Vincent

(57) ABSTRACT

The invention relates to an inductively operating sensor (1) for measuring the electrical conductivity of a fluid medium (2), having an excitation coil (3) to which an input signal is fed and a receiver coil (4) coupled to the excitation coil (3) via the fluid medium (2), the receiver coil (4) providing an output signal ($I_{Ind}$) which is a measurement of the conductivity of the fluid medium (2). The sensor (1) has means (5) for measuring a variable signal at the input of the excitation coil (3) for timely detection of damage to the windings of the excitation coil (3), the receiver coil (4), and/or to a power cable network for the sensor (1). The excitation coil (3) of the sensor is preferably fed by an input voltage ($U_{Err}$) and the means (5) for measuring the variable signal preferably measure the input current ($I_{Err}$) at the input of the excitation coil (3).

5 Claims, 1 Drawing Sheet

SENSOR FOR MEASURING THE ELECTRICAL CONDUCTIVITY OF A FLUID MEDIUM

This application is a continuation of Ser. No. 09/435,784 originally filed on Nov. 8, 1999 now abandoned, the entire disclosure of which is hereby incorporated by reference.

BACKGROUND OF THE INVENTION

The present invention relates to an inductively operating sensor for measuring the electrical conductivity of a fluid medium, having an excitation coil to which an input signal is fed, and a receiver coil coupled to the excitation coil via the fluid medium, the receiver coil providing an output signal that is a measurement of the conductivity of the fluid medium.

The excitation coil of such sensors can be designed as a toroid coil fed by an a.c. voltage. A ring-shaped alternating magnetic field is generated in the interior of the excitation coil. A receiver coil, which can also be designed as a toroid coil, is arranged in the same plane in which the excitation coil lies. The alternating magnetic field in the excitation coil causes mobile ions in the fluid medium to generate a ring-shaped current in the fluid medium to be measured, which, in turn, induces an output signal in the receiver coil whose strength is a function of the mobility and concentration of the ions, and therefore of the electrical conductivity of the fluid medium. The output signal is usually detected as an induced current.

Sensors of this type are preferably employed in factories manufacturing food or drugs for monitoring the production processes thereof. The sensors must always provide an accurate and dependable output signal to rapidly detect excessive changes in the conductivity of the medium being measured and to trigger a correspondingly rapid reaction in order to be able to prevent deterioration of the food or drugs being produced. Appropriate reactions to a change in conductivity can be triggered either indirectly via the production crews or directly by the production installation itself.

In the course of its employment, the sensor may be exposed to strong mechanical and thermal stresses that could cause damage to the windings of the excitation coil or the receiver coil. Leakage currents or even short circuits, can occur between such damaged windings and lead to distortion of the output. A short circuit between the windings renders the entire sensor unusable.

Moreover, because of the mechanical or thermal stresses on the sensor, a short circuit or a break in the sensor connection cables can also occur. Clearly, this can also lead to distortion of the output signal, or render the entire sensor unusable.

Such a distorted signal is not immediately recognized as such by the production personnel or the production installation. On the contrary, the production personnel or the production installation initially assume that the changed output signal represents a changed conductivity in the medium to be measured and the production process is accordingly modified to match the new conductivity values of the medium. Only after some time or in the event of a highly distorted output signal, is it possible to determine (for example via a plausibility check) that the output signal is distorted and that the sensor is defective. Production is normally continued prior to this determination. Therefore, the changes in the production process that occur in response to the distorted output signal can lead to the production of a defective product. As a consequence thereof, an entire production batch may have to be destroyed for safety reasons in order to dependably preclude any risk to the health of the customers due to defective food or drugs, clearly entailing considerable costs. In accordance with prior art, the detection of damage to the windings of the excitation coil, of the receiver coil, or of the sensor connection cables is not possible or only at too late a stage.

It is therefore the object of the present invention to design and further develop a sensor of the above mentioned type in such a way that it allows for early detection of damage to and associated leakage currents or short circuits in the windings of the excitation coil, the receiver coil, or the sensor connection cables.

SUMMARY OF THE INVENTION

This object of the invention is achieved with a sensor of the abovementioned kind in that the sensor has means for measuring a variable signal at the input of the excitation coil.

In accordance with the invention, it has been determined that leakage currents or short circuits caused by damage to the windings of the excitation coil or receiver coil can result in a drastic increase in the variable signal at the input of the excitation coil. If the input signal is in the form of a voltage, the input current at the input of the excitation coil may increase as a result of damage to the sensor. In this case, the means provided will measure the input current. If the input signal is in the form of a current, the input voltage at the input of the excitation coil can rise in response to damage. In this case, the means provided can measure the input voltage.

This signal at the input of the excitation coil also responds to damage to the sensor connection cables, which might lead to associated leakage currents or short circuits. The variable signal at the input of the excitation coil therefore provides rapid and dependable information regarding the ability of the sensor to function. Damage to the windings of the excitation coil or the receiver coil, or to the sensor connecting leads, which result in leakage currents or short circuits, can be detected early and dependably by monitoring this signal at the input of the excitation coil.

The production crew can react without delay to such a detected sensor defect. For example, production can initially be stopped in order to prevent manufacture of defective products. The defective sensor can be replaced with a new one and production can then be restarted. In addition, a measurement check of the conductivity of the medium being monitored can also be carried out in order to verify whether the sensor is actually defective. The shut-off and subsequent restart of production can also be performed directly by control devices of the production installation without requiring the production crew.

In accordance with an advantageous further development of the invention, the sensor has a voltage source that feeds an input voltage to the excitation coil, and the means for measuring the variable signal detect the input current at the input of the excitation coil.

The means for measuring the input current preferably have a resistor and measure the voltage dropping across that resistor. Since the voltage changes proportionally to the input current, the input current of the sensor can thereby be determined in a straightforward fashion.

In accordance with another advantageous further development of the present invention, the sensor has a measured value transformer for receiving the output signal from a receiver coil, which is connected to the means for measuring the variable signal at the input of the excitation coil, wherein the means for measuring the variable input signal generate a status signal which is a function of the measured value of the variable signal, and the means feed that status signal to the measured value transformer. In this way, the measured value transformer is always aware of the ability of the sensor to function during the measurement operation. The status signal lies within a defined threshold range as long as the sensor functions. However, if the monitored variable signal at the input of the excitation coil steeply increase or decreases as a result of damage, the means for measuring the variable signal generate an appropriate status signal, which lies outside of the threshold range. The measured value transformer can appropriately react to such a status signal without delay to thereby detect a defective sensor. In response thereto, the measured value transformer can stop the entire production to prevent manufacture of defective products.

In accordance with a preferred embodiment of the present invention, the measured value transformer corrects its output signal as a function of the strength of the status signal. If damage to the windings of the excitation coil, the receiver coil, or to the sensor connection cables only results in a slight distortion of the output signal, this will also lead to a small change in the variable signal at the output of the excitation coil. The measured value transformer can react to such a change in the variable signal with a corresponding correction of its output signal. In this manner, production can reliably continue, despite limited defects in the sensor.

In accordance with a further preferred embodiment, the measured value transformer causes a signal to be issued if the status signal lies outside a defined threshold range. This issued signal can be used to inform the production crew, which can then react accordingly. Alternatively, this signal can also constitute an alarm signal which automatically triggers defined reactions, or which stops production in the installation.

A preferred exemplary embodiment of the present invention will be explained in greater detail below with reference to the drawings.

DETAILED DESCRIPTION OF THE PREFERRED EMBODIMENT

Figure 1:
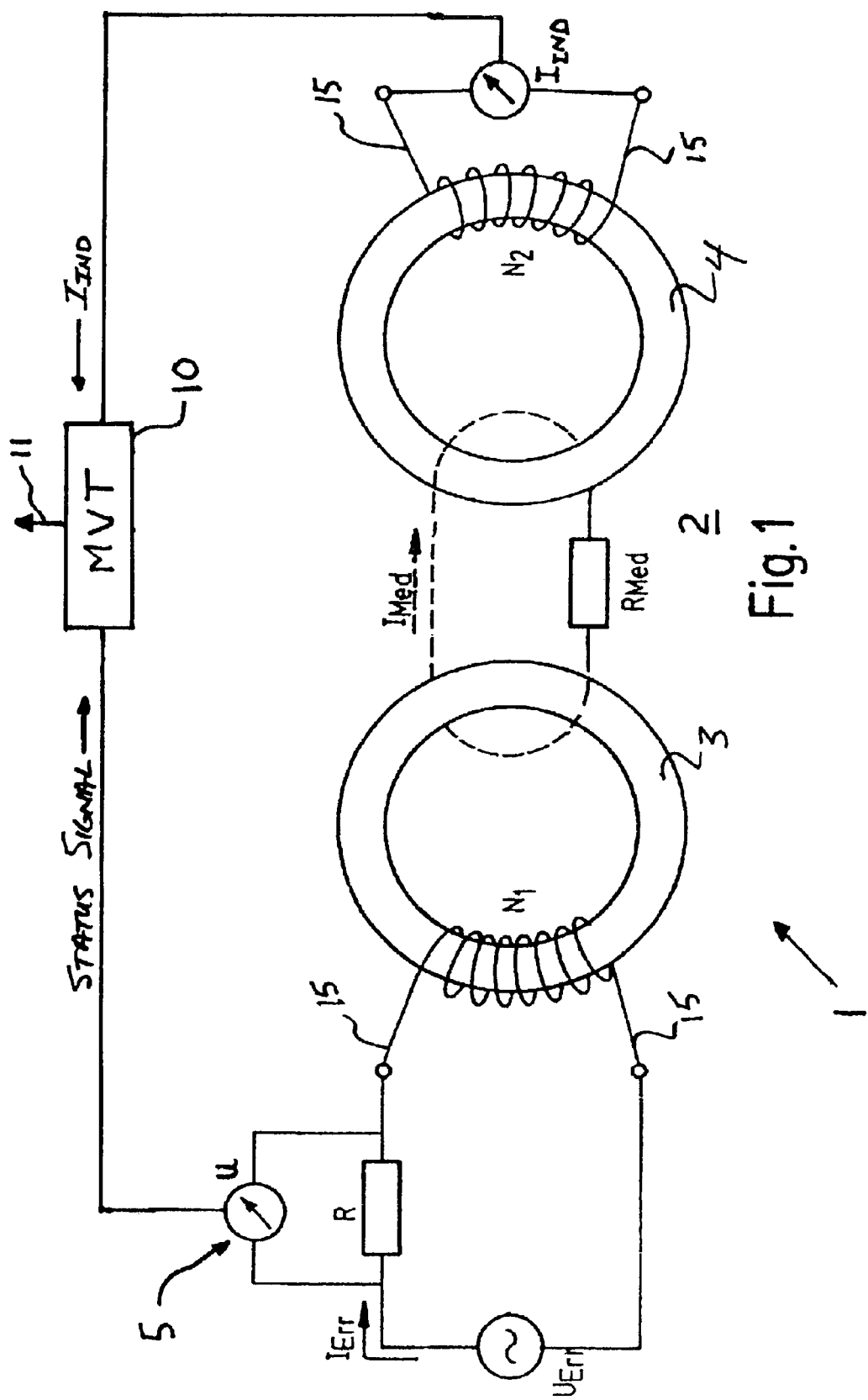
FIG. 1 shows a preferred embodiment of the sensor in accordance with the invention.

An inductively operating sensor in accordance with the invention is identified in its entirety with 1 in FIG. 1. The sensor 1 is used for measuring the electric conductivity of a fluid medium 2. The sensor 1 has an excitation coil 3 designed as a toroid coil $N_1$, which is fed by an alternating voltage $U_{Err}$. A ring-shaped alternating magnetic field is generated in the interior of the excitation coil 3. A receiver coil 4 is also arranged in the same plane in which the excitation coil 3 is located and is also designed as a toroid coil $N_2$. A ring-shaped current $I_{Med}$ is generated by ions moving in the fluid medium 2 of effective resistance $R_{med}$. In response to the alternating magnetic field in the excitation coil 3, which, in turn, generates an induction current $I_{Ind}$ in the receiver coil 4. The strength of the induction current $I_{Ind}$ depends on the mobility and concentration of the ions and therefore on the electric conductivity of the fluid medium 2.

The sensor 1 has means for measuring the input current $I_{Err}$, which are identified in their entirety by reference numeral 5. The means 5 for measuring the input current $I_{Err}$ have a resistor R and measure the voltage U dropping across that resistor R. Damage to the windings of the excitation coil 3, the receiver coil 4, or to the sensor connecting cables 15 can result in leakage currents or short circuits which can be detected early and dependably by monitoring the input current $I_{Err}$ of the excitation coil 3.

The sensor 1 also comprises a measured value transformer 10 receiving the induction current $I_{Ind}$ and connected with the means 5 for measuring the input current $I_{Err}$. The means 5 for measuring the input current $I_{Err}$ generate a status signal, which is a function of the measured value of the input current $I_{Err}$ and supply that status signal to the measured value transformer. The measured value transformer can correct the induction current $I_{Ind}$ as a function of the strength of the status signal and issue a corrected signal at an output 11 so that an error-free function of the sensor 1 is assured despite the fact that some damage to the sensor 1 has occurred. The measured value transformer can also trigger an alarm signal at output 11 should the status signal lie outside of a defined threshold range.

What is claimed is:

1. An inductively operating sensor system for measuring an electrical conductivity of a fluid medium and for monitoring the influence of leakages and short circuits, due to damage in cables and windings, on that measured conductivity, the system comprising:

means for generating an input signal;

an excitation coil;

means for connecting said excitation coil to said input signal generating means to receive said input signal;

a receiver coil coupled to said excitation coil via the fluid medium, said receiver coil generating an output signal constituting a measure of the electrical conductivity of the fluid medium;

means communicating with said input signal for detecting changes in said input signal caused by damage to at least one of said excitation coil, said receiver coil, and said connecting means; and a measured value transformer communicating with said receiver coil output signal and communicating with said input signal detecting means, wherein said input signal detecting means generates a status signal depending on a measured value of said input signal and communicates said status signal to said measured value transformer.

2. The sensor system of claim 1, wherein said input signal generating means comprises a voltage source imparting an input voltage to said input signal, wherein said input signal change detecting means detect an input current to said excitation coil.

3. The sensor system of claim 2, wherein said input signal detecting means comprises a resistor and detects a voltage drop of said input current across said resistor.

4. The sensor system of claim 1, wherein said measured value transformer corrects said receiver coil output signal as a function of said status signal.

5. The sensor system of claim 1, wherein said measured value transformer triggers an alarm signal if said status signal lies outside of an acceptable, predefined range.

* * * * *